United States Patent [19]

Furukawa

[11] Patent Number: 4,983,169
[45] Date of Patent: Jan. 8, 1991

[54] CATHETER FOR ANGIOGRAPHY

[76] Inventor: Yuichi Furukawa, 112, 2-Chome, Kamihama-Cho, Tsu-Shi Mie-Ken, Japan

[21] Appl. No.: 318,025

[22] Filed: Mar. 2, 1989

[30] Foreign Application Priority Data

Mar. 4, 1988 [JP] Japan .................................. 63-52417

[51] Int. Cl.⁵ ............................................ A61M 5/178
[52] U.S. Cl. ...................................... 604/164; 604/280
[58] Field of Search ............... 604/164, 280, 281, 282, 604/272, 273, 264

[56] References Cited

U.S. PATENT DOCUMENTS

| | | | |
|---|---|---|---|
| 4,690,175 | 9/1987 | Ouchi et al. | 604/282 X |
| 4,721,117 | 1/1988 | Mar et al. | 604/164 |
| 4,817,613 | 4/1989 | Jaraczewski et al. | 604/282 X |
| 4,841,976 | 6/1989 | Packard et al. | 604/280 X |
| 4,846,186 | 7/1989 | Box et al. | 604/164 |
| 4,863,424 | 9/1989 | Blake, III et al. | 604/282 |
| 4,863,442 | 9/1989 | De Mello et al. | 604/282 |
| 4,873,983 | 10/1989 | Winters | 604/282 X |
| 4,886,067 | 12/1989 | Palermo | 604/164 |

FOREIGN PATENT DOCUMENTS

| | | |
|---|---|---|
| 58-149766 | 9/1983 | Japan . |
| 58-218966 | 12/1983 | Japan . |
| 59-156353 | 9/1984 | Japan . |
| 60-40069 | 3/1985 | Japan . |
| 60-500013 | 9/1985 | Japan . |
| 60-212172 | 10/1985 | Japan . |

Primary Examiner—John D. Yasko
Attorney, Agent, or Firm—Armstrong, Nikaido, Marmelstein, Kubovcik & Murray

[57] ABSTRACT

The present invention relates to a catheter for angiography adapted to be used simultaneously with a catheter introducing guide wire and advanced into a blood vessel under the pilot action of the guide wire, and is characterized in that in order to secure smooth and reliable remote controllability (i.e., torque controllability) from the hand side, a high degree of flexibility precisely reflecting the movement of the guide wire and an injecting function for accurately directing a contrast agent into a target artery, the catheter is designed so that, although the catheter has, as a whole, a degree of flexiblity to enable it to follow the movement of the guide wire, its main portion in the region to be introduced into a blood vessel has a higher degree of flexibility than that of its front end portion which is shorter than the main portion.

3 Claims, 4 Drawing Sheets

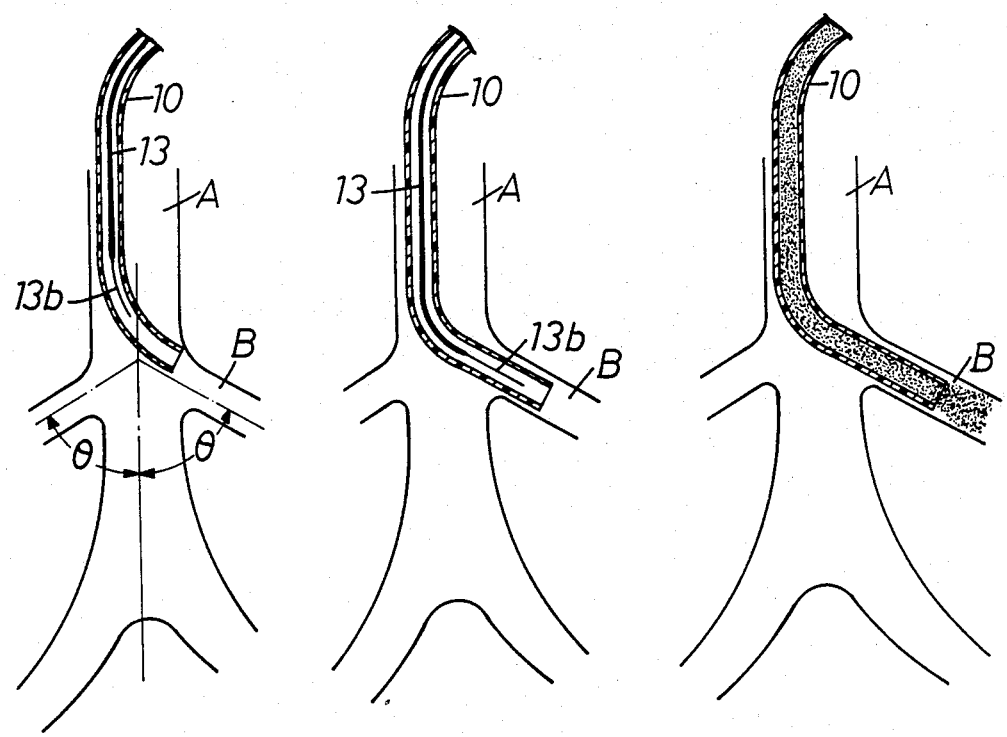
Fig. 8(I)   Fig. 8(II)   Fig. 8(III)

CATHETER FOR ANGIOGRAPHY

BACKGROUND OF THE INVENTION

DSA (Digital Subtraction Angiography) and other angiographic tests based on computer images are being used for diagnosis of vascular and tumorous diseases. In such angiographic tests, in inserting a catheter from a puncture hole in a blood vessel into a target artery, the front end of the catheter must be freely moved in the direction of travel and along curves by applying an external force on the hand side in a remote control fashion.

In recent years, it has been required to perform not only a selective operation for inserting a catheter into a primary branch of the aorta but also a super-selective operation for inserting a catheter into secondary and tertiary branches of said primary branch. Thus, a higher technique and rich experience have become indispensable for said remote control.

To secure the remote controllability (torque controllability), it has been common practice to resort to selection of a material for catheters.

That is, if such material of a catheter is soft (highly flexible), it is difficult to effect remote control on the hand side. Thus, as suggested by Japanese Utility Model Application Laid-Open Specification No. 500013/1985 (International Application PCT/US 83-864) and Japanese Patent Application Laid-Open No. 218966/1983, excluding a predetermined short region on the front end side where softness is required in view of stability of a catheter, the entire portion on the hand side is reinforced by steel wire mesh or is constructed in the form of a double tube made of materials having different entire portion on the hand side is rigid with reduced flexibility, thereby giving torque controllability to the catheter.

Making catheters slender is an adverse factor for said torque controllability, making it difficult to secure safety for remote control. For this reason, there has not been established an operating method for inserting a catheter through a puncture hole in the brachial artery, which is thin and long, for angiographic tests; at present, angiographic tests with respect to the general artery are conducted by inserting a catheter through a puncture hole in the femoral artery, which is thick.

However, it may be said that said controllability for catheters with respect to blood vessels can be secured by simultaneously using a catheter introducing guide wire which is highly flexible and which will not form a fixed bend (a so-called bending habit) even if subjected to an operating external force, said guide wire being inserted into a catheter and operated for piloting the catheter. In other words, unlike the technique resorting to the selection of a material for catheters, this idea is to look to a guide wire for torque controllability and, as it were, to reflect the controllability of the guide wire on the catheter.

In the case where such special technique is adopted, if the entire portion on the hand side is made rigid as by double-tube construction or steel wire mesh, this arrangement will destroy the superior flexibility that the guide wire possesses.

That is, in inserting a catheter into a puncture hole in the brachial artery, since, anatomically, the region extending from the sub-clavian artery via the aortic arch to the downwardly extending artery is sharply bent at less than 90 degrees, the catheter, even if made rigid, will form a corresponding bending habit under the action of body heat.

Further, in inserting a catheter into a puncture hole in the femoral artery, if this artery is abnormally bent or deformed owing to severe arteriosclerosis, the catheter inserted therein is heated by body heat and forms a bending habit corresponding to such abnormal bend.

As a result, the guide wire expected to guide the catheter correctly is "defeated" by the catheter and its inherent torque controllability is impaired, so that the catheter cannot be correctly operated until it reaches the target artery. Further, the more rigid the catheter material, the more strongly the catheter is urged against the blood vessel wall when it is retained in the blood vessel. As a result, the danger of formation of a thrombus or occlusion of blood vessel taking place increases.

In brief, when it is desired to utilize the torque controllability of a guide wire to be used for remote-controlling a catheter, it is preferable that the main portion of the catheter be made soft with high flexibility, since this makes it possible to precisely reflect the free movement of the catheter introducing guide wire; thus, the performance of the guide wire can be efficiently and reasonably developed.

On the other hand, a catheter is a medical instrument for injecting a contrast agent into a target artery. If, however, its front end portion is made soft with high flexibility, as in the known example described above, the front end portion of the catheter is subjected to the pressure under which the contrast agent is injected, swinging to and fro, with the result that the control agent cannot be injected into the target artery correctly and without loss and concentratedly. In this connection, even if a superior DSA apparatus by which target locations can be graphically represented with diagnostic contrast agent, there would be the danger of said contrast agent being misdirected.

In the case where it is desired to effect plastic working to provide an intrinsic bend suitable for the primary, secondary and tertiary branches of the artery so as to provide the front end portion of the catheter with the pilot function for inserting the catheter into a blood vessel, the softer the front end portion, the more difficult it is to form such bend in a stable manner.

Thus, so long as the above-described technique of inserting and operating a catheter to be used simultaneously with a guide wire is adopted, it is preferable that the front end portion of the catheter have the necessary minimum of rigidity (low flexibility). It goes without saying that the necessary minimum means a degree which does not hurt the blood vessel wall nor impair the torque controllability of the guide wire. It appears that a catheter for angiography meeting the necessary conditions described above has not been developed yet.

SUMMARY OF THE INVENTION

The present invention has for its object the provision of a catheter for angiography which meets such demand.

Thus, a first object of the invention is to provide an arrangement wherein while a catheter as a whole possesses a degree of flexibility which allows the catheter to follow the bending of an introducing guide wire, the main portion thereof in the region to be introduced into a blood vessel is made softer with high flexibility than its front end portion which is shorter than said main portion, whereby the movement of the guide wire is precisely reflected so that the catheter efficiently follows the movement thereof, with the torque controllability of the guide wire being developed to a maximum, and there is no danger that when the catheter changes direction or stays in a blood vessel, it forms a bending habit, not impeding the blood flow though it contacts the blood vessel wall, thus contributing to prevention of formation of a thrombus.

A second object is to provide an arrangement wherein the front end portion in the remaining region to be introduced into a blood vessel is made rigid with low flexibility, so that the front end portion of the catheter is hardly subjected to the reaction force due to spouting of a contrast agent and while maintaining a stable attitude, the catheter enables the contrast agent to be injected into a target artery correctly and without loss and concentratedly, and wherein in the case where an intrinsic bend suitable for various branches of the aorta is to be formed so as to provide the front end portion of bend can be made stably and plastically deformed.

A third object of the invention is to provide an arrangement wherein the main portion of the catheter is made soft with high flexibility and the controllability of a guide wire for introducing the same is utilized, thereby making it possible to make the catheter itself slender and hence selective and super-selective operation of catheter in connection with the trans-brachial artery (which is thin) catheterization technique.

Other objects of the present invention, together with the concrete construction of the invention, will become more apparent from the following description of preferred embodiments.

BRIEF DESCRIPTION OF THE INVENTION

FIG. 8 (I), (II) and (III) are sectional views showing the steps of insertion of a catheter into a blood vessel.

DESCRIPTION OF THE PREFERRED EMBODIMENTS

Figure 1:
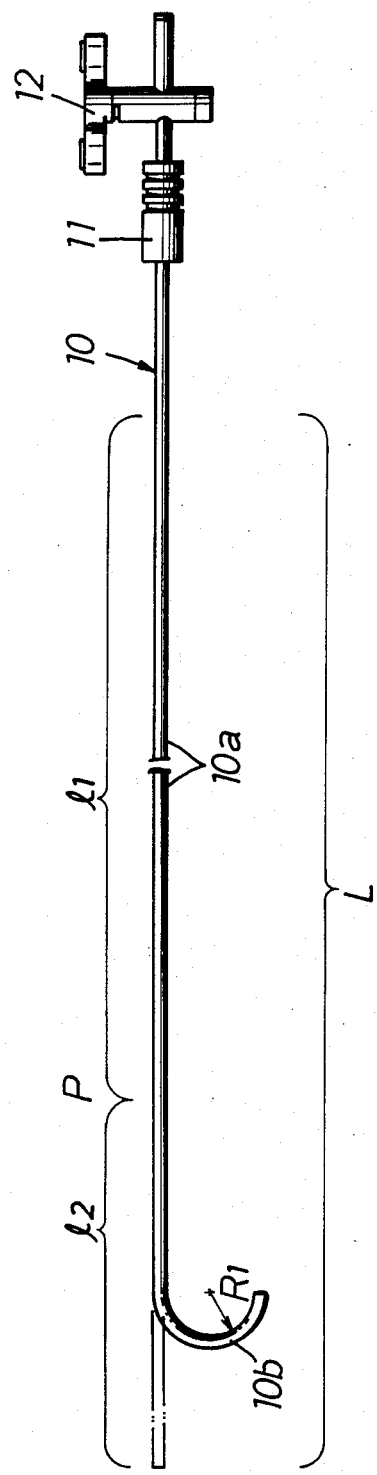
FIG. 1 is an external view, partly cut away, of a catheter for angiography according to the present invention.

In an external view shown in FIG. 1, a catheter for angiography according to the invention is collectively indicated by the numeral 10 and it is made from a synthetic resin having suitable degrees of bursting strength and flexibility, such as polyamide elastomer, polyurethane elastomer, polyester elastomer or polyethylene, into a tube form, the proximal end portion thereof on the hand side having an on-off valve 12 for contrast agent injection connected thereto through a hub or connector 11.

Figure 2:
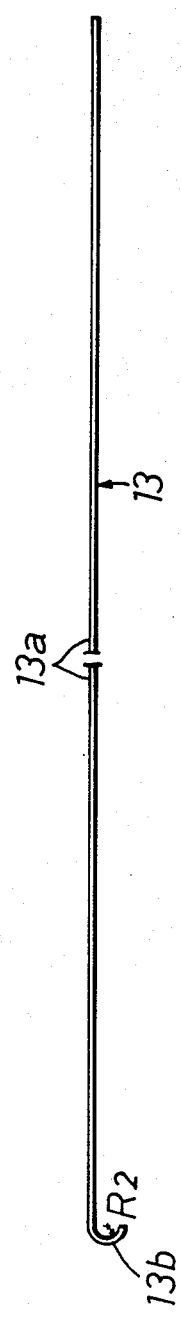
FIG. 2 is an external view, also partly cut away, of a catheter introducing guide wire to be simultaneously used with the catheter.
Figure 3:
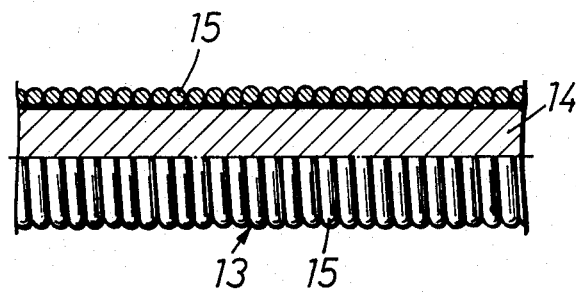
FIG. 3 is a fragmentary enlarged sectional view.

The numeral 13 in FIG. 2 collectively indicates a catheter introducing guide wire to be used simultaneously with the catheter 10. As suggested from a fragmentary enlarged sectional view in FIG. 3, the guide wire comprises a metal core wire 14 and a covering wire 15 densely wound in coil form around the outer peripheral surface thereof, and is longer than the catheter 10. Even if an operating external force for forward or rotational movement is applied to the guide wire 10 from the hand side thereof, the guide wire 10 will not form a bend (or so-called bending habit), so that its torque controllability can be transmitted to the catheter 10.

In the front end portion 13b of the guide wire 13, said core wire 14 is made gradually thin from the main portion 13a, whereby it is made soft to have the same or higher degree of flexibility than the catheter 10; thus, when it is inserted into a blood vessel, it will not hurt the blood vessel wall.

Since the overall length of the catheter 10 varies in connection with a target artery, it cannot be made constant; however, if the entire region of the catheter 10 to be inserted into a blood vessel has a fixed length comprises the catheter main portion 10a having a fixed length 11 and being made soft to have a high degree of flexibility, and the catheter front end portion 10b having a less length 12 and being made rigid to the necessary minimum degree to have a low degree of flexibility.

The necessary minimum degree means that when the catheter is inserted into a blood vessel, there is no danger of hurting the blood vessel wall and that the torque controllability of the catheter introducing guide wire used simultaneously with the catheter can be satisfactorily transmitted. That is, although the main portion 10a of the catheter 10 differs in flexibility from the front end portion 10b, the region L to be inserted into a blood vessel has a certain degree of flexibility required to follow the free bending of the guide wire 13.

As to the concrete arrangement of the catheter 10 for obtaining such change in flexibility, various forms shown in FIGS. 4 through 7 may be freely adopted.

Figure 4:
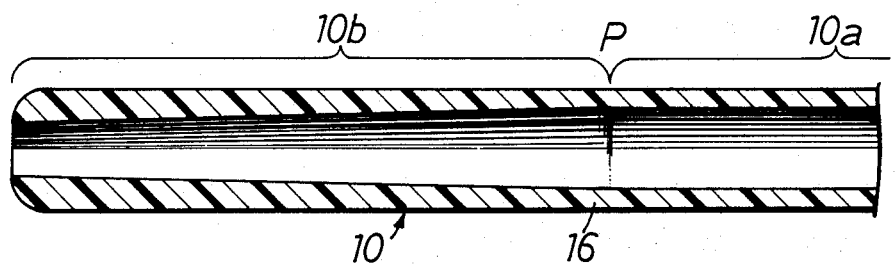
FIG. 4 is a fragmentary developed enlarged sectional view.

FIG. 4 is a fragmentary developed view of FIG. 1. In this figure, the main portion 10a of a synthetic resin tube 16 forming the whole of the catheter 10 is reduced in wall thickness, whereas the remaining front end portion 10b of the synthetic resin tube 16 is increased in wall thickness. The catheter 10 of such construction, which uses a common synthetic resin tube 16 for the main portion 10a and front end portion 10b, can be mass produced by inserting a core (not shown) in the form of a tapered conical bar into the hollow region thereof and, after molding, withdrawing said core.

Figure 5:
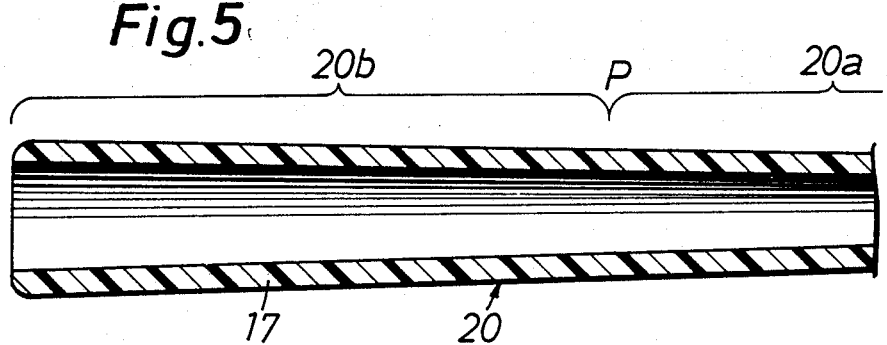
FIGS. 5 through 7 are sectional views showing various modifications of catheters corresponding to FIG. 4.

As is clear from FIG. 5 showing a first modification corresponding to FIG. 4, the wall thickness of a synthetic resin tube 17 forming a catheter 10 is uniform, but the outer diameter of the main portion 20a is small, while the front end portion 20b is large. The greater the outer diameter, the greater the bending rigidity of the catheter 10, and hence its flexibility can be made low. And the catheter 10 of such construction can be easily formed of a synthetic resin tube 17 common to the main portion 20a and front end portion 20b by using a core (not shown) in the form of a reversely tapered conical bar.

Figure 6:
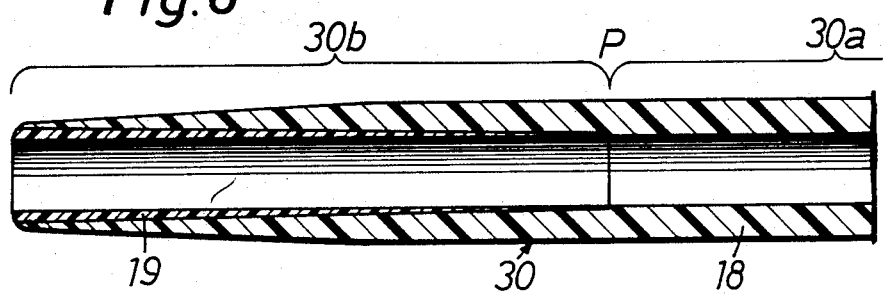

FIG. 6 shows a second modification corresponding to FIG. 4, wherein the front end portion 30b of a synthetic resin tube 18 forming a catheter 30 is integrated with a separate reinforcing tube 19 of flexible synthetic resin material in two layers, so that it is rigid with low flexibility as compared with the remaining single-layer main portion 30a in the form of a synthetic resin tube 18. Such reinforcing tube 19 can be satisfactorily integrated with the inner wall surface of the synthetic resin tube 18 forming the outer layer by heat seal or other fixing means.

Figure 7:
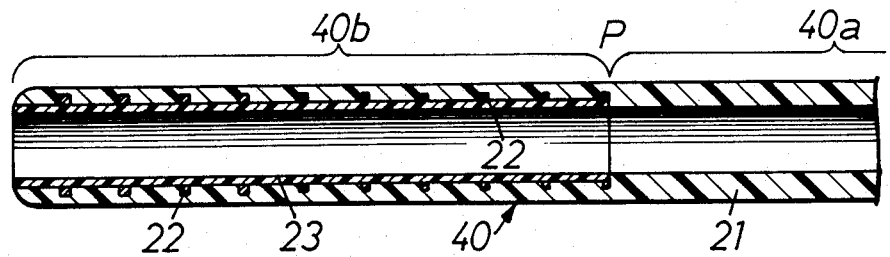

FIG. 7 shows a third modification corresponding to FIG. 4, wherein only the front end portion 40b of a synthetic resin tube 21 forming a catheter 40 is integrally lined with a separate reinforcing tube 23 of flexible synthetic resin integrally covered with non-metallic mesh 22. As a result, the front end portion 40b is made rigid, having lower flexibility than the main portion 40a. Such catheter 40 can also be easily produced by covering the outer peripheral surface successively with said mesh 22 and synthetic resin tube 21.

At any rate, since the catheter 10 in the present invention has its main portion 10a made more flexible and softer than the front end portion 10b, the catheter 10 smoothly and efficiently follows the piloting bending movement of the guide wire used simultaneously therewith and the torque controllability that the guide wire 13 possesses can be precisely reflected on the catheter 10. And there is no danger of the catheter forming a fixed bend (bending habit) when it changes its direction in a blood vessel or is retained therein; although it contacts the blood vessel wall, it does not impede the blood flow and contributes much to prevention of formation of a thrombus.

In this connection, in FIG. 1 which is a schematic view, the boundary position P between the main portion 10a and the front end portion 10b of the catheter 10 has been shown as an easily distinguishable definite demarcation line; however, as is suggested from the arrangements shown in FIGS. 4 through 7, concerning the outer diameter, inner diameter, wall thickness and the degree of flexibility of the catheter 10, it is preferable that the main portion 10a and the front end they obscurely steplessly and smoothly change to each other across the boundary position P. The reason is that with this arrangement, the above function and effect can be further improved and that the main portion 10a and the front end portion 10b of the catheter 10 can be fabricated in such a manner that they are hardly separable from each other.

On the other hand, since the front end portion 10b is made rigid by being made less flexible than the main portion 10a, it is hardly subjected to the reactive force from a contrast agent, thus making it possible to inject the contrast agent into a target artery without loss and accurately while maintaining a stable attitude resisting the spout pressure.

Further, to provide the pilot function for insertion into a target location such as a primary branch of the aorta or a sub-branch thereof, the front end 10b of the catheter 10 can be plastically deformed very easily in advance into any form as an intrinsic bend (bending habit) conforming to the target artery, and such various bent forms can be stably held.

Concerning the bent form of the front end portion 10b of the catheter 10, in FIG. 1, it is plastically deformed into an arc having a relatively large curvature radius dimension R1 which allows it to contact the inner wall of the aorta, and a shape restoring force. Thereby, it functions as a pilot for inserting the arcuate front end portion 10b into a primary branch of the aorta.

Concerning the guide wire 13 to be used simultaneously therewith, the front end portion 13b is plastically deformed into an arcuate form, as shown in FIG. 2, which has a smaller curvature radius dimension R2 than the arcuate front end portion 10b of the catheter 10 and which has a shape restoring force, thereby enabling the arcuate front end portion 13b of the guide wire 13 to function as a pilot for insertion into a secondary or tertiary branch of the aorta.

According to this, the catheter 10 is used simultaneously with the guide wire 13 and the required torque controllability is obtained from the guide wire, while the pilot function for insertion into a primary branch of the aorta is imparted to the relatively large arcuate front end portion 10b of the catheter 10 and the pilot function for insertion into secondary and tertiary branches is imparted to the relatively small arcuate front end portion 13b of the guide wire 13. As a result, there is no need to provide various intrinsic bent shapes to the front end portion 10b of the catheter 10. Furthermore, selective and super-selective catheter operation can be effected in connection with the trans-brachial artery catheterization technique while making versatile use of the catheter 10 having the relatively large arcuate front end portion 10b capable of contacting the inner wall of the aorta.

That is, FIG. 8 (I), (II) and (III) are schematic views wherein the catheter 10 described above is used for an graphic test of the renal artery B, which is a primary branch of the aorta A. In use, as shown in (I), under the pilot action of said guide wire 13, the catheter 10 is inserted into a descending artery A through a puncture hole (not shown) in the brachial artery, whereupon the front end portion 13b of the guide wire 13 is once retracted from the front end portion 10b of the catheter 10.

Then, the front end portion 10b of the catheter 10 is advanced along and in contact with the inner wall of the aorta A while retaining its arcuate bent form, until it is directed to the branch base of the renal artery B. In this case, anatomically, the branches of the descending artery A have angles of not more than 90 degrees as downward from the aorta A. Thus, according to the trans-brachial catheterization technique, the arcuate front end portion 10b of said catheter 10 can be correctly directed into a primary branch of the aorta A.

Then, as shown in FIG. 8 (II), the catheter 10 is fed by the guide wire 13, whereby the front end portion 10b of the catheter 10 advances deep into the renal artery B. Therefore, as soon as it reaches the target location, the guide wire 13 is extracted and then a contrast agent will be injected through the catheter 10 from the hand side thereof, as shown in FIG. 8 (III). Since the front end portion 10b of the catheter 10 is made more rigid with low flexibility than the main portion 10a, there is no danger of the front end portion being swung to and fro as if dancing under the pouring pressure of the contrast agent, as described above.

The above description relates to an operating method for inserting the catheter 10 into a primary branch of the aorta A. When it is desired to insert the catheter 10 into a secondary or tertiary branch of a primary branch, this can be attained, though not shown, by advancing the guide wire 13 alone from the state of Fig. (II) relative to the catheter 10, thereby exposing the front end portion 13b of the guide wire 13 from the front end portion 10b of the catheter 10.

Then, the front end portion 13b of the guide wire 13 maintains said small arcuate bent form by its own shape restoring force, thus performing the versatile pilot function of insertion into a secondary or tertiary branch; thus, under the guiding action thereof, the catheter 10 can be advanced deep into a secondary or tertiary branch. Thereafter, the guide wire 13 alone is extracted, leaving the catheter 10, through which a contrast agent is then injected, of course.

At any rate, since the main portion 10a of the catheter 10 is made soft with high flexibility, the catheter precisely follows the movement of the guide wire 13 when it is inserted over a long distance into a secondary or tertiary branch as well as when it is inserted into a primary branch of the aorta A. Therefore, the longer the distance, the more remarkably its function and effect will be developed.

When the catheter 10 is used in connection with the trans-brachial catheterization technique, it has to be longer and thinner than when it is used in connection with the trans-femoral catheterization technique. Thus, if the catheter 10 which is used simultaneously with the guide wire 13 as described above is adopted, the selective and super-selective catheter operation in connection with the trans-femoral artery (which is thin and long) catheterization technique can be performed safely and reliably by anyone without relying on high technique or much experience.

If a trans-brachial artery catheterization technique is established on the basis of the present invention, this means that angiographic tests which have heretofore been difficult for outdoor patients can be conducted, contributing much to early diagnosis of vascular and tumorous diseases and to injection of an anticancer agent into a target organ. Thus, the invention can be said to be very useful. In addition, it goes without saying that the present invention is also applicable to angiographic tests based on the conventional trans-femoral artery catheterization technique.

While the invention has been particularly shown and described in reference to preferred embodiments thereof, it will be understood by those skilled in the art that changes in form and details may be made therein without departing from the spirit and scope of the invention.

What is claimed is:

1. A remotely controlled angiography catheter device, comprising:

a catheter having a main portion and a front end portion, wherein the main portion is made softer with higher flexibility than that of the front end portion, and wherein the length of the front end portion is shorter than the length of the main position; and guide wire having a uniform diameter along the length thereof, and wherein the guide wire is inserted into the catheter for guiding the catheter when the catheter is advanced into a blood vessel.

2. A catheter for angiography as set forth in claim 1, wherein the boundary position P between the main portion (10a) and the front end portion (10b) is continuous such that the degree of flexibility changes smoothly.

3. A catheter for angiography as set forth in claim 1, wherein the front end portion (10b) of the catheter (10) has a greater radius of curvature than that of the arcuate front end portion (13b) of the guide wire (13) to be used simultaneously therewith and is plastically deformed in arcuate form for contact with the inner wall surface of the aorta.

* * * * *